United States Patent
Petit et al.

(10) Patent No.: US 8,087,285 B2
(45) Date of Patent: Jan. 3, 2012

(54) APPARATUS AND METHOD FOR A SEAL IMMERSION TEST WITH AERATED FLUID

(75) Inventors: Joan M Petit, Royal Oak, MI (US); Roy Fewkes, Farmington Hills, MI (US); Michael B Glasgow, Williamsburg, VA (US)

(73) Assignee: GM Global Technology Operations LLC, Detroit, MI (US)

( * ) Notice: Subject to any disclaimer, the term of this patent is extended or adjusted under 35 U.S.C. 154(b) by 418 days.

(21) Appl. No.: 12/474,719

(22) Filed: May 29, 2009

(65) Prior Publication Data

US 2010/0089129 A1    Apr. 15, 2010

Related U.S. Application Data

(60) Provisional application No. 61/104,394, filed on Oct. 10, 2008.

(51) Int. Cl.
*G01M 3/02* (2006.01)

(52) U.S. Cl. .................. 73/37; 73/38; 73/45.5; 73/49.7

(58) Field of Classification Search ................ 73/37, 38, 73/45.5, 49.7
See application file for complete search history.

(56) References Cited

U.S. PATENT DOCUMENTS

| | | | | |
|---|---|---|---|---|
| 4,179,920 A | * | 12/1979 | Schuller et al. | 73/86 |
| 4,267,148 A | * | 5/1981 | Dickson et al. | 422/53 |
| 5,425,266 A | * | 6/1995 | Fournier | 73/49.7 |
| 7,127,959 B2 | * | 10/2006 | Blum et al. | 73/865.6 |

* cited by examiner

*Primary Examiner* — Hezron E Williams
*Assistant Examiner* — Rodney T Frank
(74) *Attorney, Agent, or Firm* — Quinn Law Group, PLLC

(57) ABSTRACT

A test apparatus for testing fluid seals within an aerated fluid includes a container and a fluid located within the container. A plurality of seal coupons are submerged within the fluid in the container. An air supply is connected to the container to aerate the fluid within the container. Testing the seal coupons includes flowing air from the air supply through the fluid to contact the seal coupons. After the air has contacted the seal coupons then the plurality of seal coupons are removed from the fluid. A value for at least one characteristic of the seal coupons is then compared with a standard value.

11 Claims, 4 Drawing Sheets

APPARATUS AND METHOD FOR A SEAL IMMERSION TEST WITH AERATED FLUID

CROSS REFERENCE TO RELATED APPLICATIONS

This application claims the benefit of U.S. Provisional Application No. 61/104,394, filed Oct. 10, 2008, which is hereby incorporated by reference in its entirety.

TECHNICAL FIELD

The present invention relates, generally, to a standard for a seal test, and more specifically, to a standard test for immersion of a seal within a fluid.

BACKGROUND OF THE INVENTION

Commonly vehicle components require seals to protect internal operation of the component from external contamination from the environment in which the vehicle operates. The seal may come into contact with various fluids which will be located within the components during vehicle operation. Therefore, the seals are tested during the development of the vehicle with the fluids to ensure desired performance standards of the seals are maintained. The seals are tested by immersing the seal in the fluid which it may come in contact with during vehicle operation. However, during actual vehicle operation, the fluid the seal is in contact with may be aerated fluid, which may affect the performance of the seal.

SUMMARY OF THE INVENTION

A test apparatus for testing seals within an aerated fluid is provided. A seal for a type of vehicle component is to be tested within the test apparatus.

The test apparatus includes a container. A fluid of the type that is used in the vehicle component for which the seal is being tested is selected. The fluid is located within the container. The test apparatus also includes a support that is located at least partially within the container. The support is at least partially submerged within the fluid. A plurality of seal coupons are configured to be supported by the support and are submerged within the fluid in the container. The plurality of seal coupons are formed from a predetermined seal material that is being tested. The test apparatus also includes an air supply that is connected to the container to aerate the fluid within the container.

A method of testing the seal material includes providing the fluid within the container. After the fluid is in the container then a plurality of the seal coupons are suspended in the fluid. Following this, testing the seal material includes flowing air through the fluid to contact the seal coupons. After the air has contact the seal coupons then the plurality of seal coupons are removed from the fluid. A respective value for at least one characteristic for each of the plurality of seal coupons is then compared with a standard value for the at least one characteristic.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Figure 1:
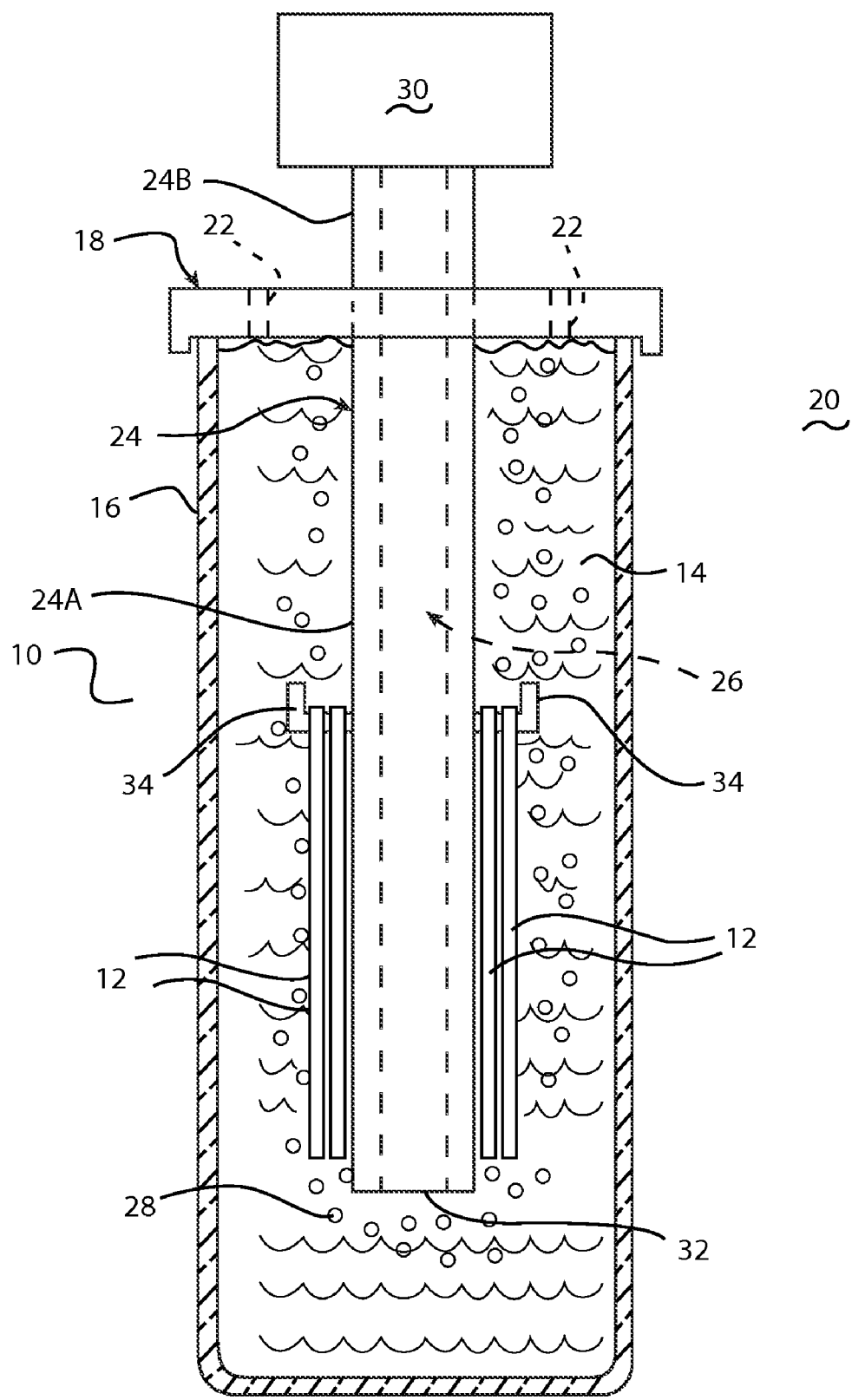
FIG. 1 is a schematic perspective illustration of a test apparatus for a seal test with an aerated fluid.

Referring to the Figures, wherein like reference numbers refer to the same or similar components throughout the several views, FIG. 1 schematically illustrates a test apparatus 10 for testing a seal coupon 12 within a fluid 14. The seal coupon 12 is formed from a predetermined material that provides a seal for a vehicle component during vehicle operation. For example, the seal coupon 12 is formed from the pre-determined seal material which seals an automatic transmission for a vehicle, such as clutch piston seals. The fluid 14 would then preferably be an automatic transmission fluid. Other combinations may also be used from various driveline seal materials and fluids.

The test apparatus includes an external container 16. The external container 16 is preferably glassware. For example, the external container 16 may be the type used with the ASTM D6594 standard titled, "Evaluation of Corrosiveness of Diesel Engine Oil at 135 C".

The test apparatus 10 also includes a container cover 18 to protect the container 10 from any contamination of a test environment 20. The container cover 18 may include at least one vent 22 to equalize the pressure within the container 10 to the test environment 20.

A support 24 extends through the container cover 18 to support a plurality of the seal coupons 12. The support 24 is preferably tubular in shape and defines a passage 26. The passage 26 provides air 28 from a supply source 30. The supply source 30 may be an oxygen tank, or a supply of filtered air from the test environment 20. Air 28 from the supply source 30 flows through the passage 26 to a passage opening 32. The air 28 flows out of the passage 28 at the passage opening 32 where it is mixed with the fluid 14. The air 28 rises through the fluid 14 and passes over the seal coupons 12.

The seal coupons 12 are suspended in the fluid 14 by hooks 34 extending from the support 24. The hooks 34 are located in a vertical position on the support 24 that prevents the seal coupons 24 from contacting the container 14 and allows for the seal coupons 12 to be completely submerged within the fluid 14.

The support 24 includes a first portion 24A which is located within the container 12. The first portion 24A of the support 24 is formed from a rigid material such as glass or steel to provide support for the seal coupons 12 on hooks 36. The material of the first portion 24A is selected to ensure the material will not have an effect on the fluid 14 within the container 12 during the test. A second portion 24B of the support 24 is located externally of the container 12. The second portion 24B may be formed from the same material as the support 24 or from a different material. The second portion 24B of the support 24 or a portion of the second portion 24B may be formed from a flexible material, such as rubber tubing, to allow a flexible connection between the supply source 30 and the container 12. If the first portion 24A and the second portion 24B are formed of different materials, the connection between the first portion 24A and the second portion 24B may be located externally of the container 12. Alternatively, the connection between the first portion 24A and the second portion 24B may be located internally of the container 12 in such a manner that the second portion 24B is not in contact with the fluid 14, i.e. above the fluid line within the container 12.

Figure 2:
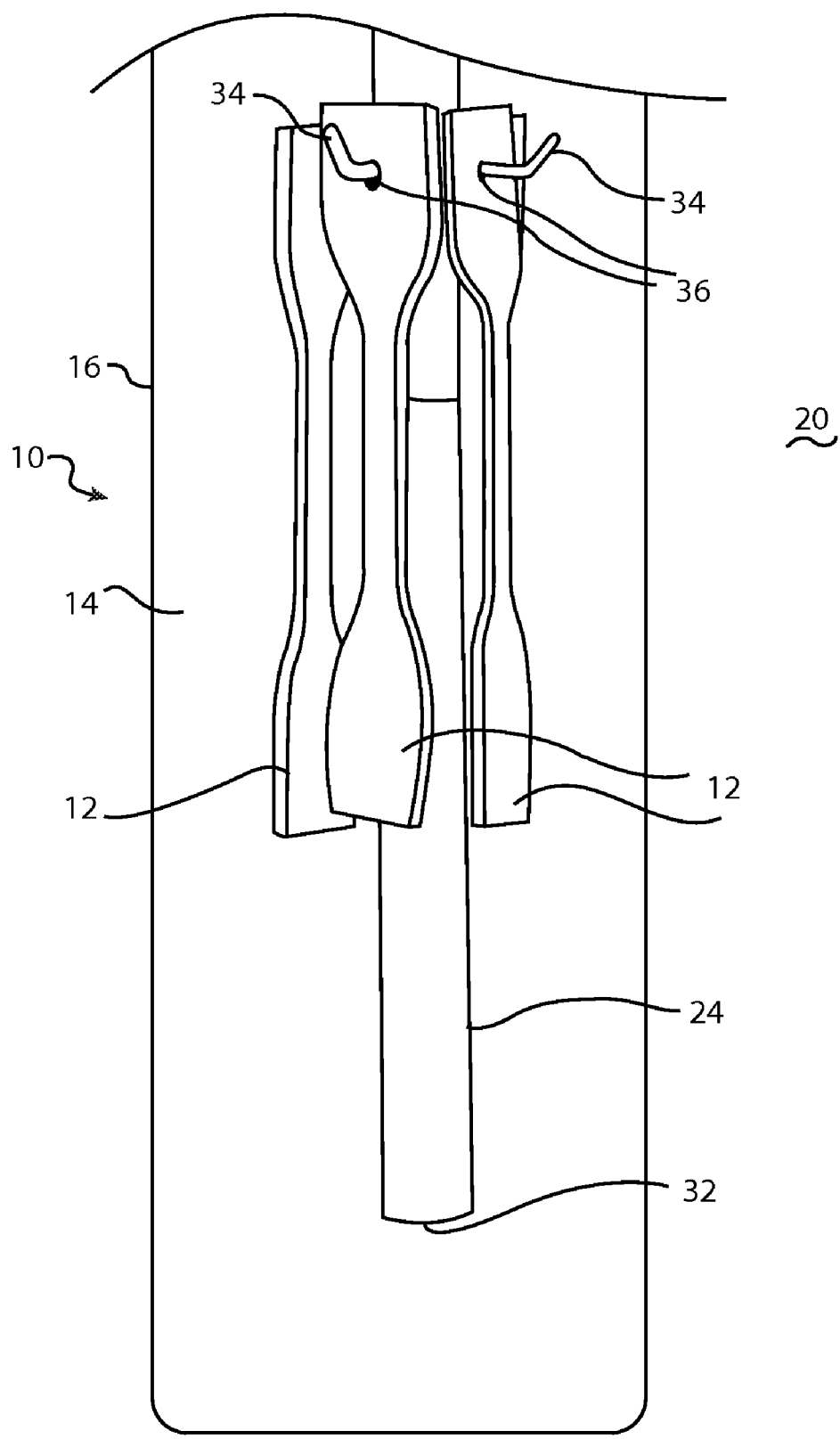
FIG. 2 is an enlarged schematic perspective illustration of a plurality of seal coupons in the test apparatus of FIG. 1.

FIG. 2 is an enlarged schematic perspective illustration of a plurality of seal coupons 12 in the test apparatus 10. Multiple seal coupons 12 may be located on each hook 34. In the embodiment shown, there are four hooks 34 each having two seal coupons 12. Therefore, the test would provide eight samples for analysis upon completion. The seal coupons 12 for a particular trial of the immersion test are all formed from the same material. To compare various combinations of the material for the seal coupons 12 and the fluid 14, additional immersion tests may be run with the desired combination to provide new samples.

Figure 3:
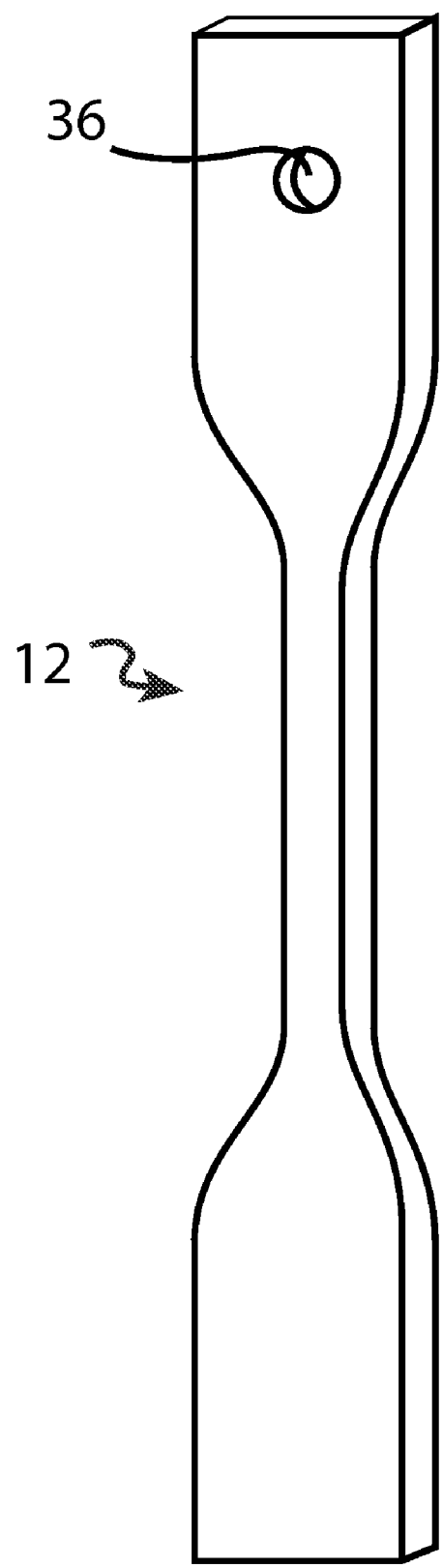
FIG. 3 is a schematic perspective illustration of a seal coupon for use within the test apparatus of FIGS. 1 and 2.

Referring to FIG. 3, an example of a seal coupon 12 is illustrated. The seal coupon 12 includes a coupon opening 36 for hanging the seal coupon 12 on the hooks 34 (shown in FIG. 2). The seal coupon 12 is formed of the seal material for which the test is desired. As discussed above, there are typically multiple seal coupons 12 for each test cycle to provide multiple test samples. The seal coupons 12 may be prepared according to an existing standard, such as ASTM D3183 standard titled, "Practice for Rubber—Preparation of Pieces for Test Purposes from Products."

Figure 4:
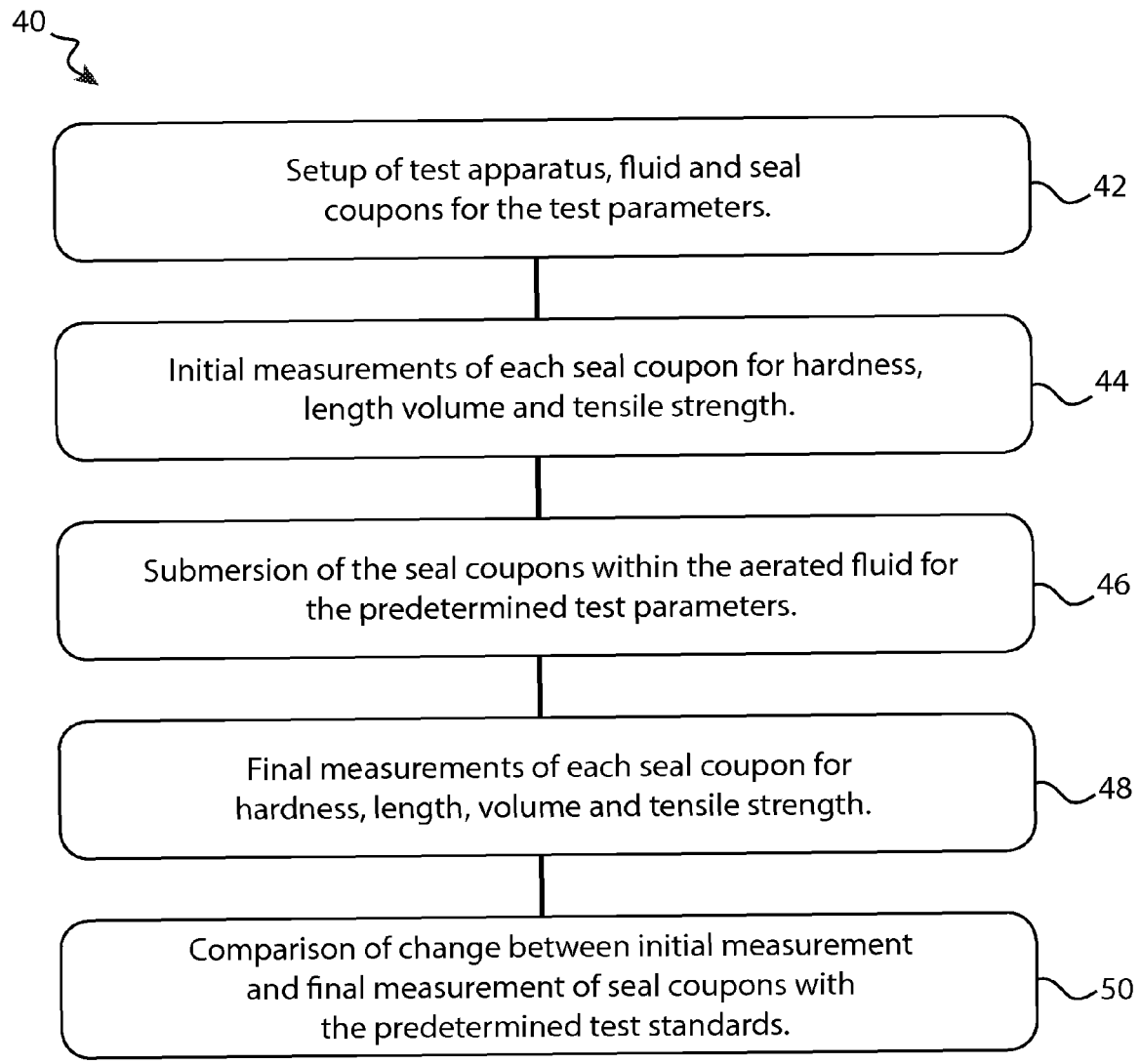
FIG. 4 is a flowchart illustration of a test operation for use with the test apparatus of FIGS. 1-3.

Referring to FIG. 4, an example embodiment of a process for completing the aerated fluid seal immersion test is described. The aerated fluid seal immersion test operation 40 is begun, step 42, by setting up the test apparatus 10, fluid 14 and preparing the seal coupons 12 according to the test parameters. The test parameters may include, but are not limited to, the type of fluid 14, the seal material for the seal coupon 12, temperature of the fluid 24, the amount of fluid 14, the flow rate of the air 28 through the fluid 14, etc. One test parameter would be the amount of time the seal coupons 12 are immersed, for example, one hundred hours. An additional test parameter may include a temperature of the test fluid 14 for the duration of the test, for example 150 degrees Celsius. This may typically be done by heating the test environment 20 (shown in FIG. 1) to a predetermined temperature. The test parameters may be based on the fluid 14 being tested, the material of the seal coupon 12 being tested or on some combination thereof.

The seal coupons 12 are initially measured, step 44, for at least one initial material characteristic. Preferably, an initial value for each sample of the seal coupons 12 is determined for a plurality of material characteristics. The material characteristics measured may include but are not limited to, a hardness (or Durometer), tensile strength, length of the coupon, and volume of the coupon.

After measuring the initial material characteristics, the seal coupons are then left in the test apparatus 10 for the predetermined time as identified by the test parameters, step 46.

Upon completion of the test parameters, each of the seal coupons 12 are removed from the test apparatus. The seal coupons 12 are again measured for final material characteristics, step 48. The final material characteristics which are measured are the same characteristics for which the seal coupons 12 were initially measured. These final measurement values for each material characteristic are then compared, step 50, with the initial measurement values for each material characteristic. The changes between the initial and final measurement values are compared to a predetermined standard value for each material characteristic.

While the best modes for carrying out the invention have been described in detail, those familiar with the art to which this invention relates will recognize various alternative designs and embodiments for practicing the invention within the scope of the appended claims.

The invention claimed is:

1. A test apparatus comprising:
    a container;
    a fluid for a vehicle component located within the container;
    a support located at least partially within the container and at least partially submerged within the fluid;
    a plurality of seal coupons, formed from a predetermined seal material corresponding the vehicle component, wherein the plurality of seal coupons are configured to be supported by the support and submerged within the fluid; and
    an air supply for the container to aerate the fluid within the container.

2. The test apparatus of claim 1, wherein the support defines a passage and air flows through the passage to the fluid within the container.

3. The test apparatus of claim 1, wherein the support includes a plurality of hooks to maintain the plurality of seal coupons within the fluid.

4. The test apparatus of claim 1, wherein the plurality of seal coupons are not in contact with the container when the seal coupons are supported by the support.

5. The test apparatus of claim 1, wherein at least a portion of the air within the fluid is in contact within the plurality of seal coupons when the seal coupons are supported by the support.

6. A method of testing a seal material for use in a vehicle component comprising:
    providing a fluid within a container, wherein the fluid is for use in the vehicle component;
    suspending a plurality of seal coupons in the fluid, wherein the seal coupons are formed from a predetermined seal material for use with the fluid in the vehicle component;
    flowing air through the fluid to contact the seal coupons with at least a portion of the air;
    removing the plurality of seal coupons from the fluid; and
    comparing a respective value for at least one characteristic for each of the plurality of seal coupons with a standard value for the at least one characteristic.

7. The method of claim 6, further comprising:
    measuring at least one characteristic for each of the plurality of seal coupons for an initial characteristic value prior to suspending the plurality of seal coupons within the fluid; and
    measuring at least one characteristic for each of the plurality of seal coupons for a final characteristic value after removing the plurality of seal coupons from the fluid.

8. The method of claim 7, wherein said at least one characteristic is one of a seal coupon hardness, a seal coupon length, a seal coupon volume, and a seal coupon tensile strength.

9. The method of claim 6, wherein said flowing the air through the fluid further comprises, providing air from an air supply and flowing the air through a passage at least partially defined by the support to the fluid within the container.

10. The method of claim 6, wherein flowing the air through the fluid further comprises maintaining a constant flow of air.

11. The method of claim 6, wherein said providing the fluid further comprises heating the fluid to a predetermined temperature and wherein suspending the seal coupon further comprises leaving the seal coupon submerged within the fluid for a predetermined amount of time.

* * * * *